United States Patent [19]

Stewart et al.

[11] 4,013,413
[45] Mar. 22, 1977

[54] APPARATUS AND METHOD FOR RAPID ANALYSES OF PLURALITY OF SAMPLES

[75] Inventors: Kent K. Stewart, Silver Spring; Gary R. Beecher, Laurel; Peter Edgar Hare, Takoma Park, all of Md.

[73] Assignee: The United States of America as represented by the Secretary of Agriculture, Washington, D.C.

[22] Filed: July 10, 1975

[21] Appl. No.: 594,893

[52] U.S. Cl. .......................... 23/230 R; 23/253 R; 23/259; 73/422 GC
[51] Int. Cl.² ................... G01N 1/00; G01N 31/00
[58] Field of Search ............... 23/253 R, 259, 292, 23/230 R; 73/422 GC, 423 A; 141/130

[56] References Cited

UNITED STATES PATENTS

| | | | |
|---|---|---|---|
| 3,356,458 | 12/1967 | Steinle et al. | 23/253 R X |
| 3,479,880 | 11/1969 | Mutter et al. | 73/422 GC |
| 3,489,011 | 1/1970 | Firman et al. | 73/422 GC |
| 3,501,961 | 3/1970 | Hable et al. | 73/422 GC X |
| 3,521,674 | 7/1970 | Dodson et al. | 73/422 GC X |
| 3,690,833 | 9/1972 | Ferrari | 23/253 R X |
| 3,858,450 | 1/1975 | Jones | 73/422 GC X |
| 3,881,872 | 5/1975 | Naono | 23/253 R |

Primary Examiner—Joseph Scovronek
Attorney, Agent, or Firm—M. Howard Silverstein; William E. Scott; David G. McConnell

[57] ABSTRACT

An apparatus and method for automatically analyzing up to 150 samples per hour with high precision. Air segmentation and its concomitant limitations and drawbacks are eliminated by use of a novel stream sampling valve which transfers a predetermined volume of sample only from a sample flow system to a reaction flow system.

8 Claims, 13 Drawing Figures

APPARATUS AND METHOD FOR RAPID ANALYSES OF PLURALITY OF SAMPLES

This invention relates to an apparatus and a method for rapid analysis of discrete samples. More particularly, it relates to an apparatus and a method for quantitatively analyzing a series of individual samples rapidly and precisely.

Presently available instruments or apparatus for the quantitative analysis of individual samples use of air segmented sample stream and operate at a maximum speed of 10 to 20 samples per hour with only moderate precision. This type of apparatus is described in U.S. Pat. Nos. 2,879,141 and 3,241,432. If one is not concerned with time and precision, the prior art apparatus is quite adequate. However, we feel that there is a great need for a method and apparatus with which samples can be analyzed rapidly and precisely.

Therefore, it is an object of this invention to provide an apparatus and a method for analyzing samples rapidly and with very high precision.

Another object is to provide an apparatus and method that maintains sample integrity without air segmentation.

Still another object is to provide an apparatus and method that is particularly useful to scientists, physicians and clinical and other technicians for colorimetric, fluorometric, spectrophotometric and other types of instrumental analyses.

A further object is to provide an apparatus and method for accomplishing the above objectives in which the sample flow system and the reaction flow system are separate entitles connected only by a sampling means.

A still further object is to provide an apparatus and method for rapid and precise instrumentation analyses in which the sampling means automatically transfers a predetermined amount of sample from the sample flow system to the reaction flow system thereby eliminating the need for air or gas segmentation.

Another further object is to provide an apparatus and method according to the above objectives that is equipped with recording means to automatically record the results of the instumental analyses.

In general, according to this invention the above object are accomplished by an apparatus having two separate flow systems, a sample flow system to transport solutions of samples, interspaced by air and wash solution, from the sampler to a stream sampling means and a reaction flow system to mix the sample with reagent and to analyze and record the results. The sample flow system is provided with a wash solution reservoir, a sampler or sample holding device which positions the proper sample in place for transfer into the system, a sample probe for alternately introducing wash solution, air, sample and air into the system, a withdrawal pump to provide suction for the probe and a waste tank to dispose of excess liquid. The reaction flow system is provided with a sample solvent reservoir and a pump to transfer the solvent into the system, one or more reagent reservoirs with pumps to transfer the reagent(s) into the system, a mixer, reaction and cooling coils, instrumentation such as a colorimeter, a fluorometer or other measuring means and means for recording and automatically processing acquired data. The two systems have one common element, the stream sampling means by which a sample is automatically transferred from the sample flow system to the reaction flow system where it is mixed and reacted with reagent and analyzed instrumentally. This means of transferring a sample from one system to another system is provided by our stream sampling valve. This valve is made from four four-way valves, each of which has four ports and an element slidably mounted for movement within the valve. The slider element, which at any given moment during operation of the apparatus is, for all practical purposes, in one of two positions, the load position, that is, when it removes or takes a sample from the sample flow system, or the inject position, that is, when it injects the sample into the reaction flow system, is provided with fluid conducting conduits adapted to register with the ports in the four-way valves. Since the travel time between the two positions must be rapid enough to cause no changes in pressure in the reaction flow system, the load and inject positions are the only positions that are of any consequence to the successful operation of the apparatus. Those positions that the valve momentarily occupies during the change from load to inject or vice versa can safely be ignored without adversely affected the operation of the apparatus. The stream sampling valve is also provided with a plurality of coils (five in the preferred embodiment) that connect to ports on and are external to the four four-way valves. These serves to transport fluids to and from the four-way valves. The position of the slider elements control the flow of fluid through the valve conduits and through the coils.

Referring to drawings.

Figure 1:
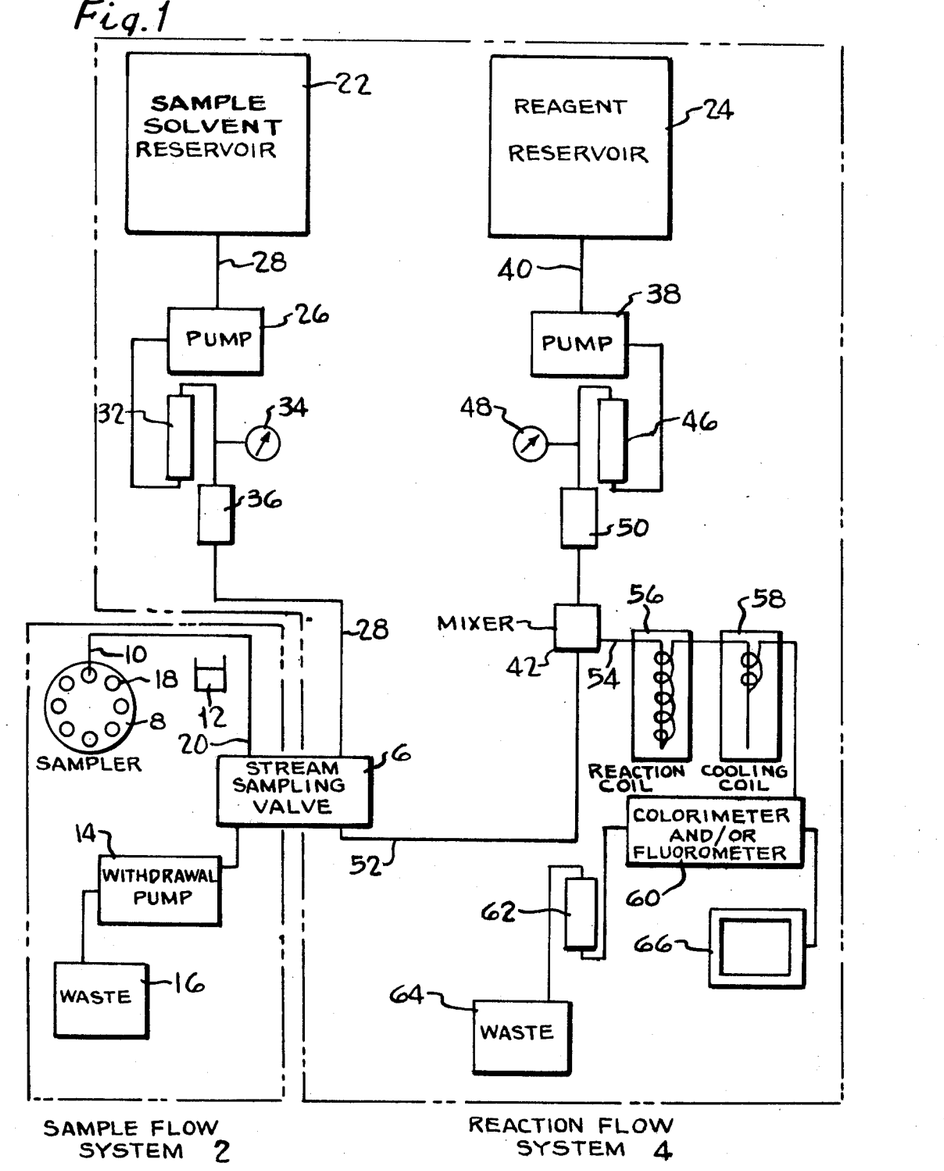
FIG. 1 is a schematic representation of the system and apparatus of the present invention.

The invention is schematically represented in FIG. 1 which shows that it is comprised of two separate systems, the sample flow system 2 and the reaction flow system 4, connected by one element common to both systems, stream sampling valve 6.

Sample flow system 2 is provided with a sampler or sample holder 8, sample probe 10, wash solution reservoir 12, peristaltic withdrawal pump 14, and waste tank 16. Sample holder 8 is a circular or rotary plate having provision for holding a plurality of sample cups or tubes 18 as illustrated in FIG. 1. Sample holder 8 is operated by an of a number of suitable commercially available means that rotate or index it intermittently so that such cup or tube 18 is moved, in succession, into take-off position for sample probe 10 to remove a portion of the sample. Sample probe 10 is also operated by any commercially available suitable mechanism to withdraw, in alternating sequence, a portion of sample from the tube 18 that is in take-off position at that moment, then a portion of wash solution from reservoir 12, then a portion of the sample in the next succeeding tube 18, and so forth until all of the samples have been analyzed. Since pump 14 operates continuously, air is drawn into probe 10 during the time that the probe moves from sample to wash solution and again when it moves back to the next sample. Consequently, samples and wash solution are separated from each other by a segment of air. More specifically, successive samples are separated from each other by individual segments of air, wash solution and air. Sample flow system 2 and more specifically probe 10 is connected to stream sampling valve 6 by fluid conduit 20 through which samples, wash solutions and air segments are conducted to valve 6 and also through which wash solutions, air segments, and portions of samples not removed from sample flow system 2 by stream sampling valve 6 are withdrawn through pump 14 to waste tank 16.

Reaction flow system 4 is provided with a sample solvent reservoir 22 and one or more reagent reservoirs 24. Solvent from reservoir 22 is pumped by pulse free liquid pump 26 through fluid conduit 28 to stream sampling valve 6. Conduit 28 is provided with flow meter 32, pressure gauge 34 and filter and bubble trap 36 between pump 26 and stream sampling valve 6. Reagent is pumped from reservoir 24 by pulse free liquid pump 38 through fluid conduit 40 to mixer 42. Conduit 40 is provided with flow meter 46, pressure gauge 48, and filter and bubble trap 50 between pump 38 and mixer 42. Samples cut out of conduit 20 by valve 6 and sample solvent cut out of conduit 28 by valve 6 are conducted through fluid conduit 52 to mixer 42. The mixed liquids then flow through fluid conduit 54 to reaction coil 56, to cooling coil 58 to colorimeter or other type of instrument for analytical purposes 60 and then through flow meter 62 to waste tank 64. As the stream of liquid flows through instrument 60, recorder 66 continuously records the color, fluorescene or other property of the fluid stream that is being measured.

As previously stated, an important feature of this invention is the fact that sample flow system 2 and reaction flow system 4 are separate entities and because of this, air or gas segmentation is eliminated in the reaction system. The common element of the two systems is stream sampling valve 6 which automatically transfers a predetermined amount of sample from sample flow system 2, or, more precisely, from fluid conduit 20, to fluid conduit 52 in reaction flow system 4.

Figure 2:
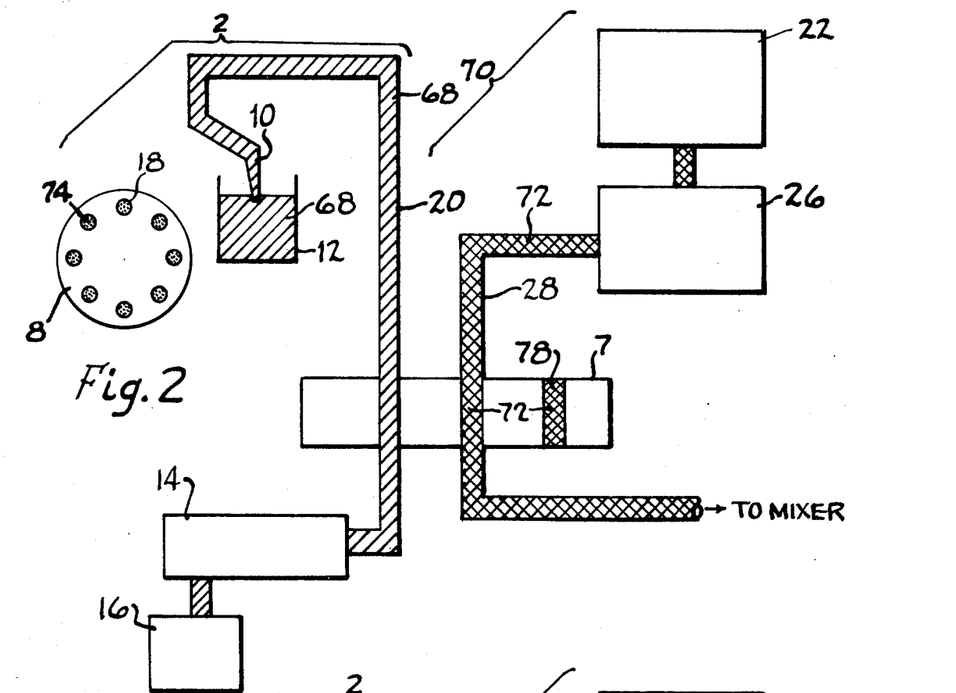
FIGS. 2 to 7 are schematic representations illustrating, in successive steps, operation of the stream sampling valve.
Figure 3:
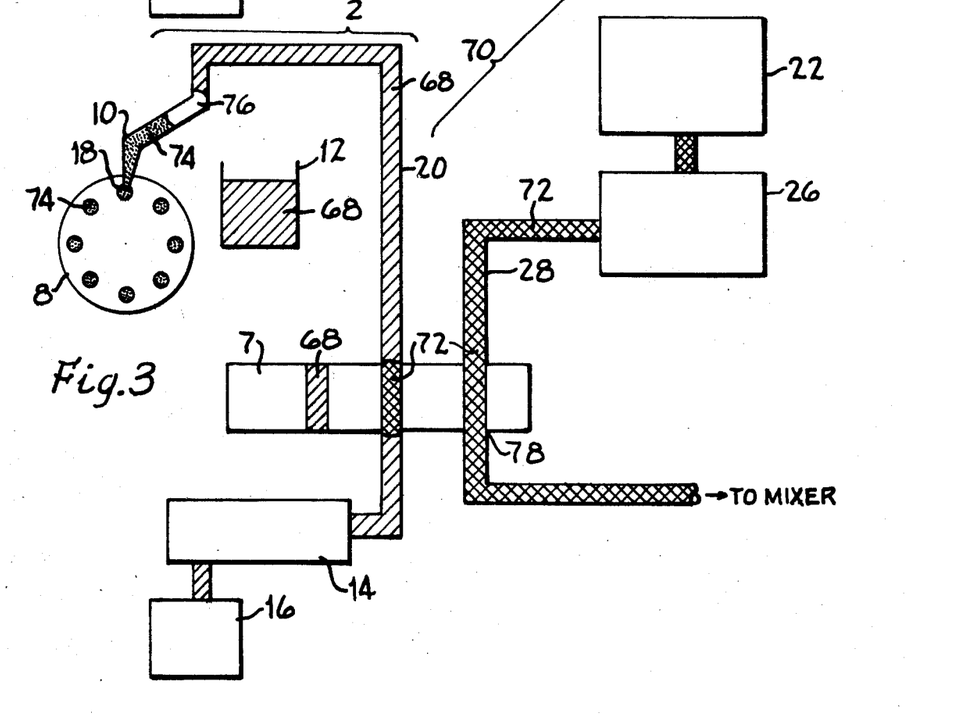
Figure 4:
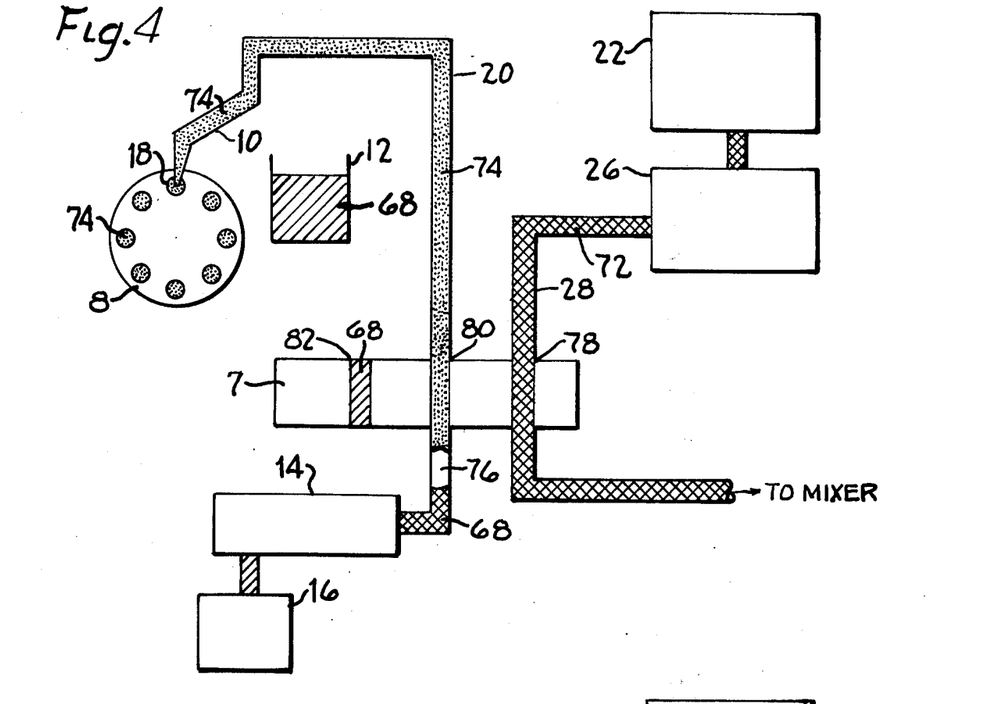
Figure 5:
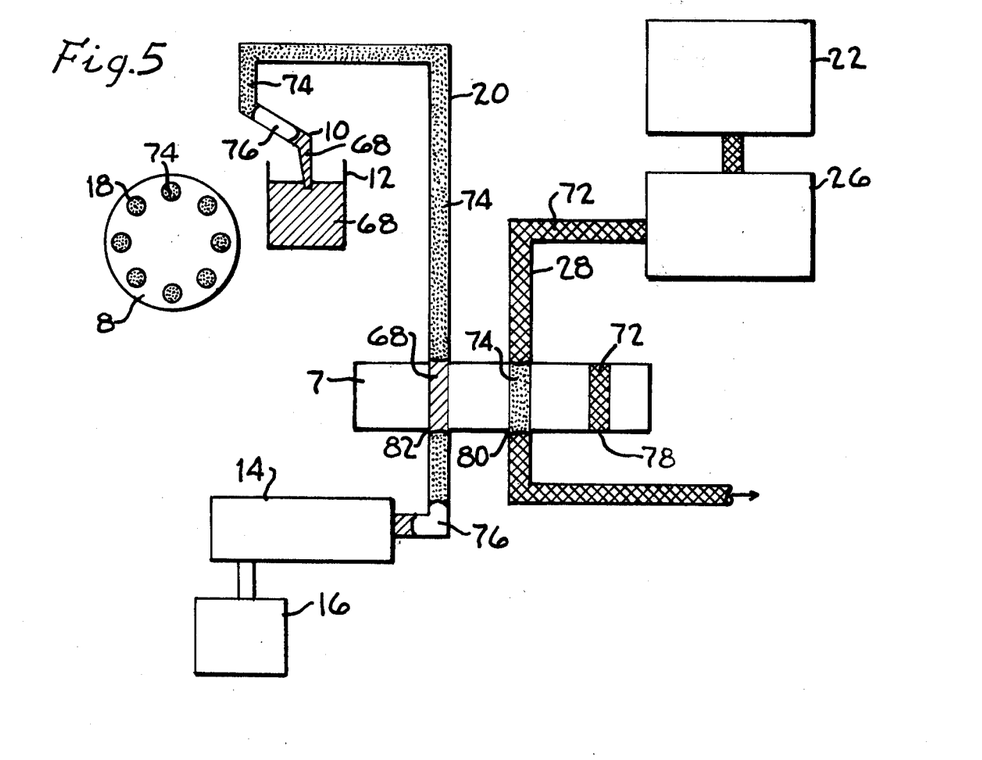
Figure 6:
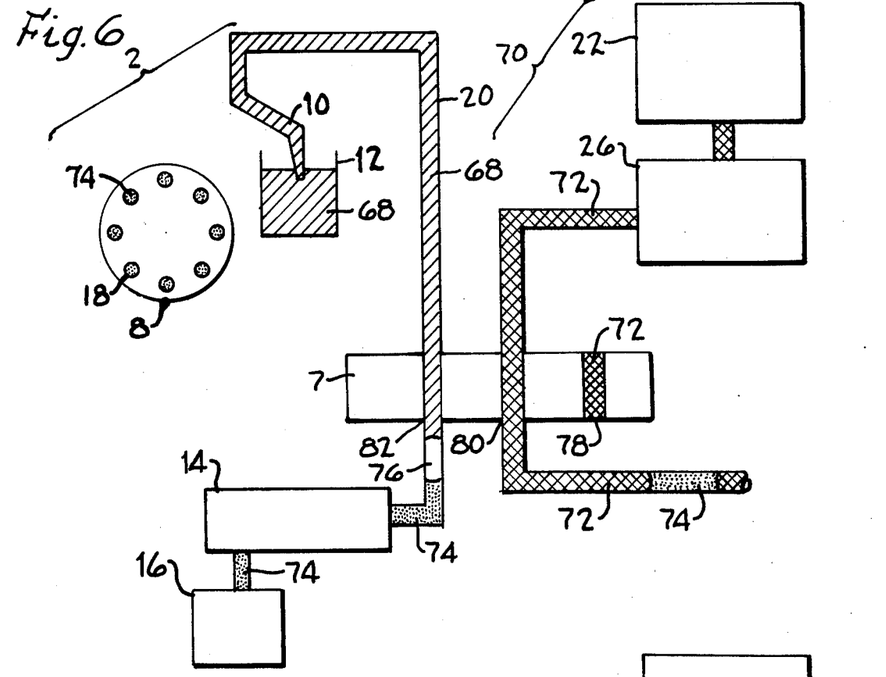
Figure 7:
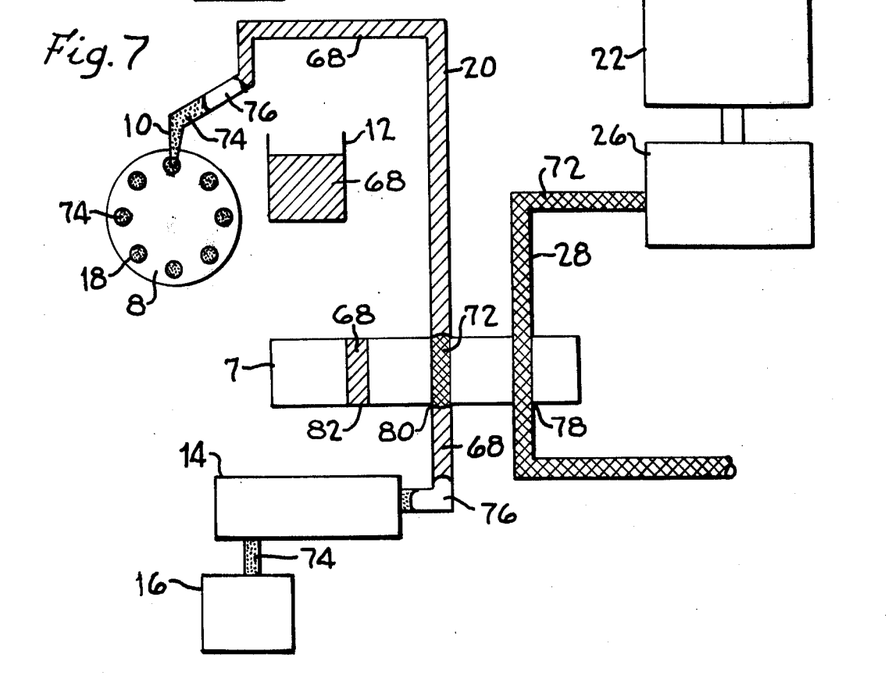

Steam sampling valve 6 is an important and critical part of this invention. The function of this valve is to slice out a measured volume of the sample from fluid conduit 20 of sample flow system 2 and inject this sample into the reaction flow system. It is important that only the sample and neither the air nor the wash solution be injected into reaction system 4. A schematic representation of this process is illustrated in FIGS. 2-7, where only the slider element 7 of valve 6 is represented. In FIG. 2 the system is shown in its prerun condition. Both pumps 14 and 26 are pumping, probe 10 is in the wash reservoir 12, sample flow system 2 is filled with wash solution 68, sample solvent portion 70 of reaction flow system 4 is filled with sample solvent 72 and stream sampling valve slider element 7 is in right hand position which when transferring a sample is the inject position. At the time for the first sample, sample probe 10 is moved from wash reservoir 12 to the first sample cup 18 and immediately after the probe is in place, valve slider element 7 moves rapidly to the left hand position which when transferring a sample is the load position. The situation is now represented by FIG. 3. The first sample solution 74 is withdrawn from sample cup 18 in sampler 8 by suction supplied by withdrawal pump 14 into sample probe 10 and then into conduit 20 of sample flow system 2. Since withdrawal pump 14 works continuously, when sample probe 10 moves from wash reservoir 12 to a sampler 8 a bubble of air 76 is introduced into sample flow system 2. Thus, at this time, there is sample being sucked into sample flow system 2 and this sample 74 is separated from wash solution 68 by a bubble of air 76. Sample solvent 72 is pumped from the sample solvent reservoir 22 by its positive displacement pump 26 through fluid conduit 28 then through passage 78 of valve slider element 7 and then on to mixer 42. After a given time has elapsed the situation is that shown in FIG. 4. Wash solution 68 and air bubble 76 have passed through passage 80 of valve slider element 7 and passage 80 is now filled with sample 74. Passage 82 is filled with wash solution 68 and is in a dead position. Passage 78 is filled with sample solvent 72. At this time the sample probe 10 is moved from sample cup 18 in sampler 8 to wash reservoir 12 while simultaneously sampler 8 indexes to the next cup 18. After probe 10 has moved, slider element 7 is moved rapidly to the right. The situation is now that shown in FIG. 5. Sample probe 10 while moving from sample cup 18 to wash reservoir 12 sucks in some air and thus fluid conduit 20 has wash solution 68 separated from sample solution 74 by air bubble 76. Passage 78 of valve slider element 7 is in a dead position, passage 80, containing sample solution 74 is now part of sample solvent portion 70 of system 4 and the passage 82 has moved into the sample flow system 2. The sample now travels through the solvent stream to the mixer where it is mixed with the reagent. At the same time the wash solution washes out fluid conduit 20 and after a set time the situation is that shown in FIG. 6. Air bubble 76 and sample solution 74 have traveled past the valve slider element 7 and the passage 82 is filled with wash solution 68, passage 80 is filled with sample solvent 72 and the passage 78 is still in a dead position. At this time sample probe 10 is moved from wash reservoir 12 to a new cup 18 in sampler 8. After probe 10 has moved valve slider element 7 is moved rapidly to the left. The situation is now that shown in FIG. 7. Sample probe 10 while moving from wash reservoir 12 to sample cup 18 has sucked in some air and thus conduit 20 has sample solution 74 separated from the wash solution 68 by air bubble 76. Passage 82 containing wash solution 68 is in a dead position, passage 80 containing sample solvent 72 is now in sample flow system 2 and passage 78 is now in sample solvent portion 70 of reaction flow system 4. The system will now continue to cycle on to the situation shown in FIG. 4 and the cycle will continue through operations described above until the sampler stops. The actual operation of the valve 6 and valve slider element 7 is more complicated than shown in the above schematic representations because several requirements must be met. These requirements will be discussed following the description of FIGS. 8-13.

We found that commercial valves of the type shown in FIGS. 2-7 had excessive mixing volumes and thus were not suitable for our purposes. Conseqeuntly, we discovered that we could make a steam sampling valve that met our requirements by connecting four four-way valves as shown more or less diagrammatically in FIGS. 8-13. We found that use of these valves in the arrangement shown made it easy to change coils. We used sample coils in sizes ranging from 1 to 100 µl because these sizes suited our purpose. However, other sizes may be used. Although the valves can be connected in many different ways, we preferred the arrangement shown in FIGS. 8-13 to illustrate our invention. The valves used in the apparatus were pneumatic actuated valves operated by electrically controlled solenoid air valves to effect slider movement. The timer that is used to drive the sampler and sample probe was connected through an appropriate rectifier to also actuate the solenoid air valves. The selected portion of the sample flow system to be sampled was controlled by the withdrawal rate of the withdrawal pump and the gauge and length of tubing in the sample flow system.

Figure 8:
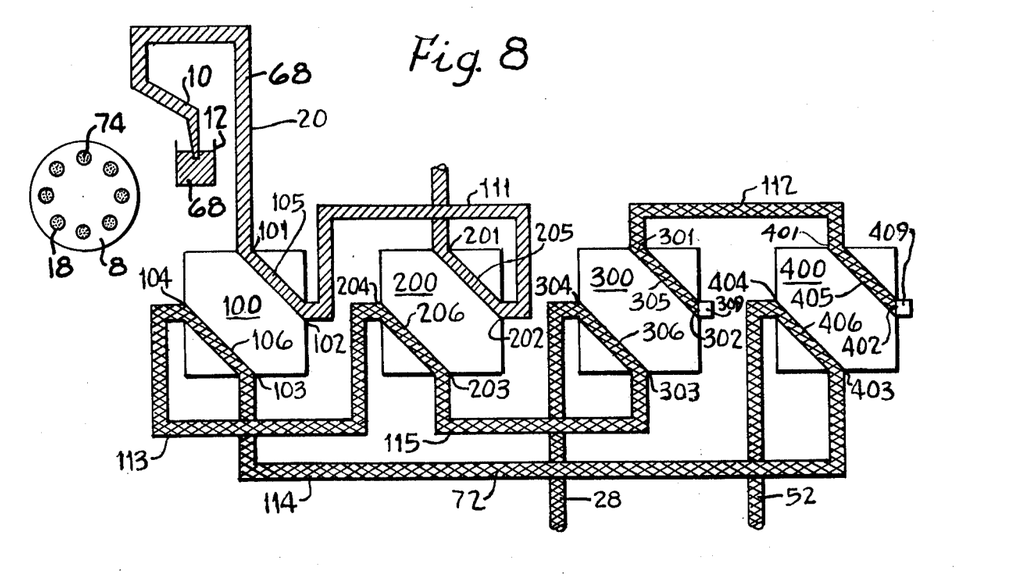
FIGS. 8 to 13 illustrate the four component four-way valves of the stream sampling valve and how their passageways are connected to transfer a sample from the sample flow system to the reaction flow system.

The sequence of events described schematically in FIGS. 8–13 is conceptually the same sequence of events described in FIGS. 2–7. The only difference is that the four four-way valves, 100, 200, 300 and 400 of the stream sampling valve are shown as they are connected to each other and to the other parts of the high speed analyzer. The valves are physically assembled so that the slider elements 7 (not shown in FIGS. 8–13) of the four-way valves act in concert and change position simultaneously. At any given time during operation of the apparatus, each slider element 7 is in one of two positions as previously described with reference to FIGS. 2–7. Each valve is provided with four ports which, in conjunction with the slider elements in each valve, form interconnecting passageways or conduits through which fluid flow is routed. The position of the sliders control fluid flow. For ease of identification the ports and interconnecting conduits in each valve are numbered in the same hundred series as the valve number. For example, the first port of valve 100 is numbered 101, the third port of valve 300 is numbered 303 and the conduit connecting the first and second ports (201 and 202, respectively) of valve 200 is numbered 205. When the slider elements 7 are in the first or load position, which exists when sample probe 10 is in a sample cup 18 of sampler 8, ports 101, 201, 301 and 401 are connected to ports 104, 204, 304 and 404, respectively, and ports 102, 202, 302, and 402 are connected to ports 103, 203, 303 and 403, respectively. When the slider elements 7 are in the second or inject position, which exists when sample probe 10 is in wash reservoir 12, ports 101, 201, 301, and 401 are connected to ports 102, 202, 302, and 402, respectively, and ports 103, 203, 303, and 403 are connected to ports 104, 204, 304 and 404, respectively. In FIG. 8, the system is shown in its prerun condition. Pumps 14 and 26, see FIG. 1, are operating, probe 10 is in wash reservoir 12, the valve slider elements are in the second position, and wash solution 68 flows through probe 10 and fluid conduit 20 to port 101, through conduit 105 to port 102, through coil 111 to port 202, through conduit 205 to port 201 and then to withdrawal pump 14 and waste tank 16. Sample solvent 72 flows from reservoir 22 by the action of pump 26 through conduit 28 to port 304, through conduit 306 to port 303, through coil 115 to port 203, through conduit 206 to port 204, through coil 113 to port 104, through conduit 106 to port 103, through coil 114 to port 403, through conduit 406 to port 404, and then to mixer 42. At this stage of the operation, sample solvent 72 in conduits 305 and 405 and in coil 112 is in a static condition. Plugs 309 and 409 are provided to prevent escape of fluid.

Figure 9:
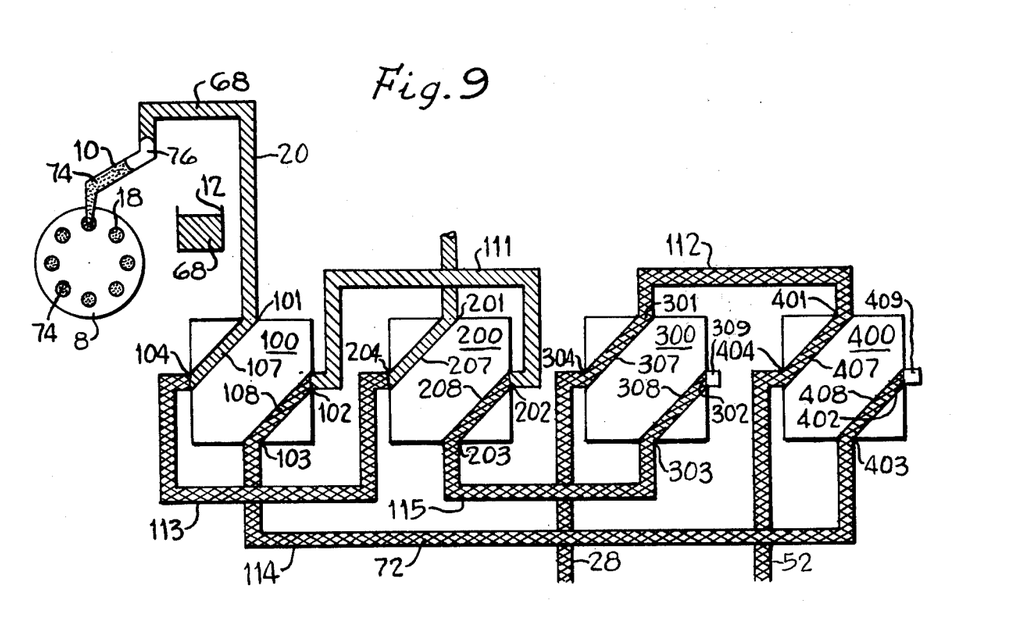
Figure 10:
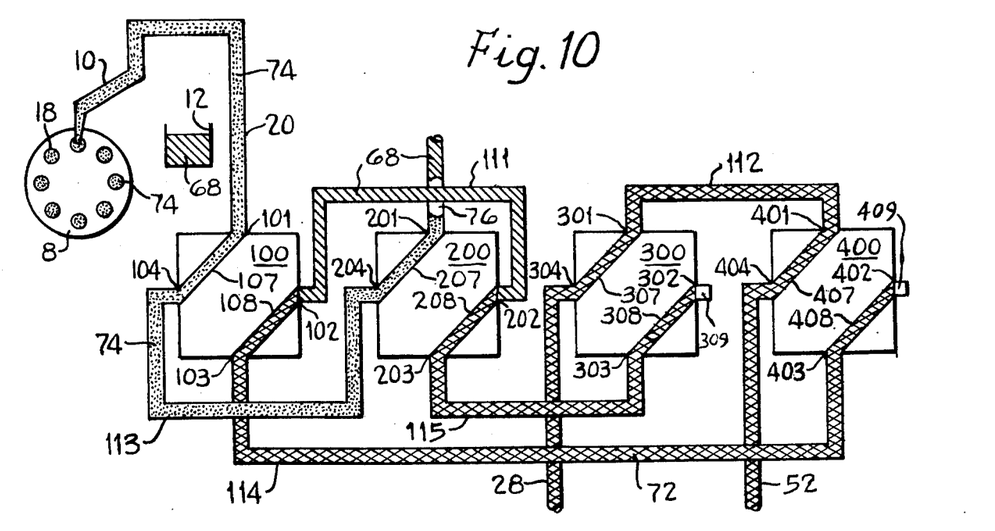

When it is time to introduce the first sample into the system, probe 10 moves from wash reservoir 12 to the first sample cup 18. Immediately after probe 10 is in position to take a sample 74 from cup 18, valve slider elements 7 move into the first position and the system is operating in the mode as represented in FIG. 9. In moving from reservoir 12 to cup 18, probe 10 sucked in air thus providing air bubble 76 between wash solution 68 and sample 74. The sample stream which has wash solution 68 and air bubble 76 in front of it, flows through conduit 20 to port 101, through conduit 107 to port 104, through coil 113 to port 204, through conduit 207 to port 201, and then to withdrawal pump 14 and waste tank 16. Sample solvent 72 from reservoir 22 is pumped by 26 through conduit 28 to port 304, through conduit 307 to port 301, through coil 112 to port 401, through conduit 407 to port 404 and through conduit 52 to mixer 42. The remainder of the system, that is, coils 111, 114 and 115 and conduits 108, 208, 308, and 408, is static and contains the solutions indicated in FIG. 9. The operating mode and condition of the system some time later, that is, just before probe 10 moves from cup 18 to reservoir 12, is shown in FIG. 10. Air bubble 76 has moved through valves 100 and 200 and is heading toward withdrawal pump 14 and waste tank 16, conduits 107 and 207 and coil 113 are filled with sample 74. The rest of the system is the same as shown in FIG. 9.

Figure 11:
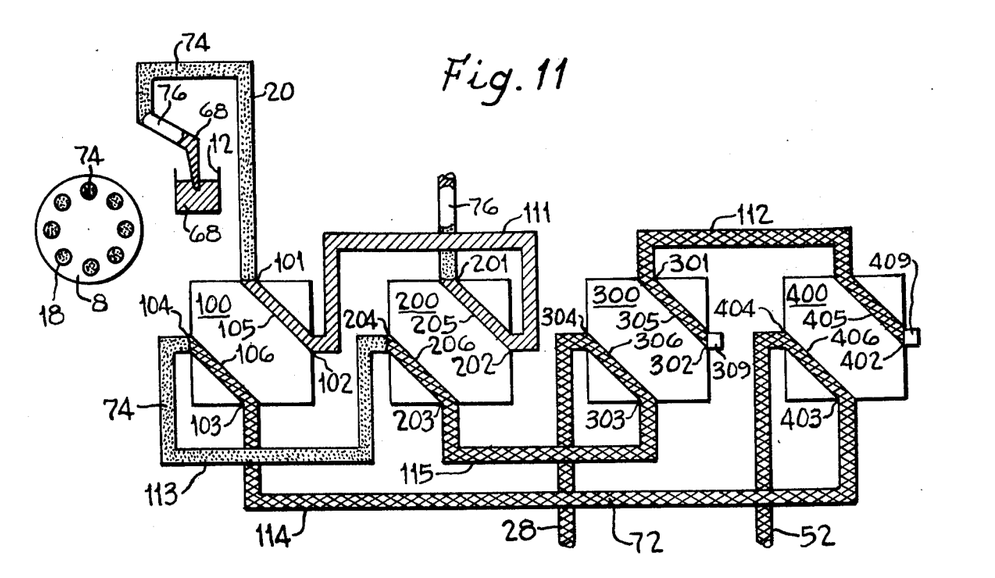

At this point, sample probe 10 moves from sample cup 18 to wash reservoir 12 and slider elements 7 move to the second position. As probe 10 moves to reservoir 12, sampler 8 indexes one position forward to put the next cup 18 in position for sampling. The system is now operating in the mode as represented in FIG. 11. Probe 10 has just started to pick up wash solution 68 which is separated from sample 74 by air bubble 76 which was picked up as probe 10 moved from sampler 8 to reservoir 12. The sample stream is now flowing through conduit 20 to port 101, through conduit 105 to port 102, through coil 111 to port 202, through conduit 205 to port 201, and then to withdrawal pump 14 and waste tank 16. Sample solvent 72 from reservoir 22 is pumped by 26 through conduit 28 to port 304, through conduit 306 to port 303, through coil 115 to port 203, through conduit 206 to port 204, through coil 113 which at this point contains an accurately measured portion of the sample only, to port 104, through conduit 106 to port 103, through coil 114 to port 403, through conduit 406 to port 404 and then through conduit 52 to mixer 42. Solvent 72 in coil 112 is static at this operating stage.

Figure 12:
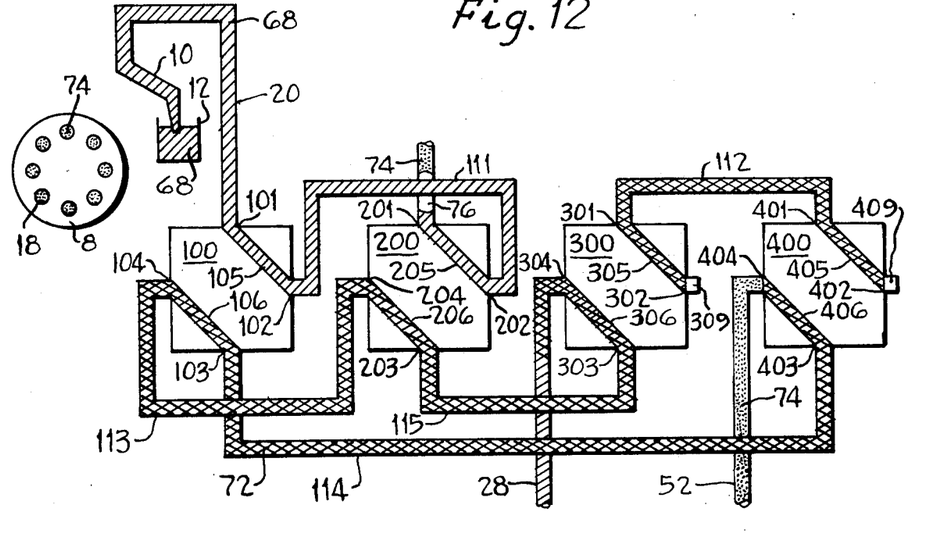

The condition of the system just before probe 10 moves back to sampler 8 is shown in FIG. 12. Wash solution 68 has washed out of valves 100 and 200 all of sample 74 and air bubble 76 has just emerged from port 201 on its way to pump 14 and waste tank 16. Solvent 72 has pushed the accurately measured portion of sample 74 from coil 113 through conduit 106, coil 114, and conduit 406 to conduit 52 through which it flows to mixer 42. Thus, transfer of an accurately measured sample from the sample flow system to the reaction flow system has been accomplished.

Figure 13:
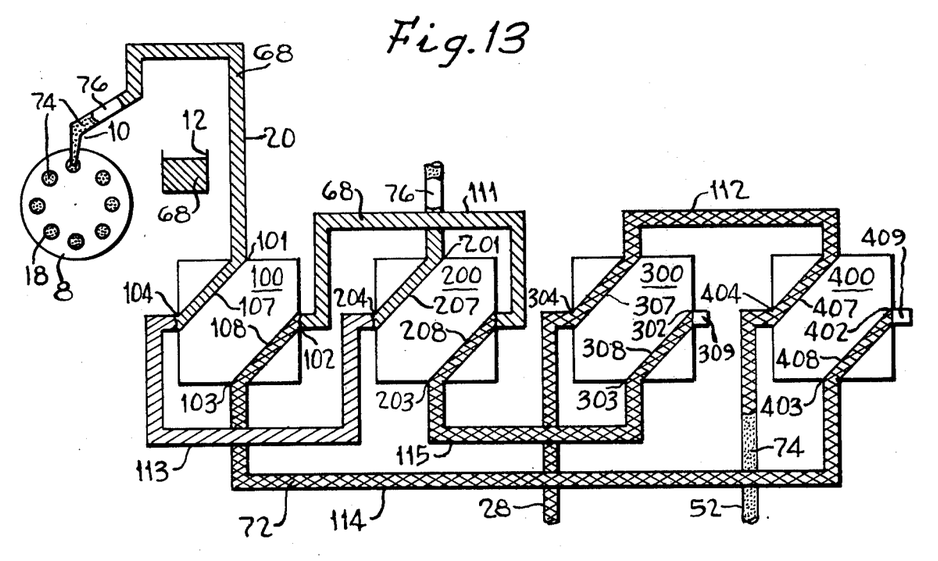

Probe 10 now moves to sampler 8 to introduce the next sample into the system. When probe 10 is ready to take the next sample, slider elements 7 move to the first position and the operating mode of the system is shown in FIG. 13. The cycle just described is repeated as many times as is necessary to analyze all the samples.

In order to meet our objectives and attain very high precision, we discovered that certain requirements in construction and in functioning had to be met. One of the first requirements was that the apparatus function is such a manner as to provide baseline readings between samples even at high rates of analysis. Although baselining could be accomplished by using the well-known air segmentation technique, it could only be done at low rates (10-30 samples per hour) of analyses. At high rates of analyses (60-150 samples per hour) using the air segmentation technique, baseline readings were not attained. Consequently, there was a considerable loss of precision. Constructionwise, the conduits and coils through which the sample flows in the stream sampling valve and in the reaction flow system must have a small or narrow bore and be made of material inert to the fluids flowing through them. Conduits and coils having internal diameters of from about 0.028 to about 0.009 inches, that is, 22 to 32 American Wire Gauge (AWG), are quite suitable for the purposes of this invention. Those having an internal diameter of about 0.018 inches (26 AWG) are preferred.

Inert materials suitable for use in constructing the stream sampling valve and the conduits and are polytetrafluoroethylene (Teflon) and polychlorotrifluoroethylene (Kel F).

The stream sampling valve must be designed, constructed, and timed to transfer a known, predetermined volume of sample only from the sample flow system to the reaction flow system. The mixing volumes in the stream sampling valve must be very small. In our preferred mode of the apparatus no mixing or an extremely inconseqential amount of mixing takes place in the stream sampling valve. As described with reference to FIGS. 8-13, our stream sampling valve was constructed from four four-way valves in which the slider elements were pneumatically actuated. This means of actuating the sliders is not essential; any means, electronic, mechanical or other actuating source, is suitable provided that it will actuate the sliders to operate rapidly and make the necessary change of port connections in less than 2 seconds. The preferred time required for the sliders to make a change of port connections is the smallest fraction of a second approaching zero time. Rapid movement of the sliders is desirable so that the movement will not cause changes in pressure in the reaction flow system. In addition, the actuating means must be connected to a timing device so that the valve is fired at the proper time to transfer sample solution only and not air or wash solution from the sample flow system to the reaction flow system. It is understood, of course, that the timing of the valve firing is coordinated with rate of sample withdrawal, conduit bore size, and other factors that affect the flow the flow of liquid through the sample flow system. The stream sampling valve must also be constructed so that the sample flow system is washed out while the sample is being injected into the reaction flow system. In order to eliminate flow variations and the resultant loss of precision, the four four-way valves must be connected so that there is equal pressure to flow when the sliders are in either the load position or the inject position so that the flow rate is constant, regardless of the position of the valve sliders.

The narrow bore conduits and coils already discussed are conducive to a desired high flow rate through the reaction flow system. Although the preferred flow rate presently ranges from 1 to 8 ml per minute, flow rates covering a range from 0.1 to 25 ml per minute are attainable with the apparatus of this invention. However, even with the narrow bore conduit and coil system, we could not attain high flow rates and precision if the connecting fittings were such that they allowed mixing of fluids, Consequently, all connecting fittings in the apparatus must be no dead volume fittings, that is, ones that will maintain sample integrity by providing no extra volume in which the flowing liquids can mix.

The pumps that deliver sample solvent and reagents into the system must be pulse free, liquid delivery pumps capable of delivering liquid at 50 to 50 psi with combined flow rates of at least 120 ml per hour, and a delivery precision of ±1.0% of delivered volume.

The mixer, where the sample solvent stream joins the reagent stream, must provide good mixing of the two streams and yet maintain sample integrity. This has been attained by using T-type no dead volume mixture. Other no dead volume mixers may also be used. The only requirements are that they provide good mixing and maintain sample integrity.

Since the reaction product being measured, whether it be color or some other measurable entity, is devloped in the reaction coil, the coil must be long enough for the reaction to take place. The apparatus of this invention has been successfully used with coils from about 10 to 100 feet long. However, the invention is not limited to that range of lengths. The only requirement is that it be long enough for the sample and reagent to react. The internal diameter of the reaction coil should be the same as that of that of the conduits and coils to which it is connected in the reaction flow system in order to maintain sample integrity.

The cooling coil is used to cool the flowing liquid from the reaction coil to the temperature of the colormeter or other analytical instrument if necessary. The internal diameter of the cooling coil should be the same as that of the reaction coil.

In order to continue maintaining the sample integrity until the desired analytical results are obtained and recorded, the colorimeter, fluorometer, or other analytical instrument must be equipped with a low volume flow cell with a fairly long optical path length. Flow cells having optical path lengths of from 0.1 to 60 mm and cell volumes of from less than 1 $\mu l$ to 20 $\mu l$ have been successfully used in the apparatus of this invention.

Flow meters and pressure gauges are used in the reaction flow system to measure flow rates and presures In-line filters are used to remove dust and particles and bubble traps are provided to remove air bubbles. The only requirements for these parts of the apparatus are that they perform their intended functions.

The apparatus of this invention as just described is useful for the analysis of up to 150 samples per hour with high precision. In fact, with respect to precision at high rates of analysis, we found the average coefficient of variation to be slightly less then 1.0%.

We claim:

1. An apparatus for rapidly analyzing a plurality of fluid samples, comprising a sample flow system for introducing samples into the apparatus, a reaction flow system into the apparatus, a reaction flow system for introducing reagent and sample solvent into the apparatus and for reacting reagent and sample and analyzing the reacted sample, said reaction flow system having means for providing a continual flow of fluid at a constant rate through said system when the apparatus is in operation, and a stream sampling valve common to both the sample flow system and the reaction flow system for transferring a volume of sample only from the sample flow system to the reaction flow system, comprising a plurality of four-way valves, each having a plurality of ports and an element slidably mounted for movement within said valves, said elements being provided with fluid conducting conduits adapted to register with the aforesaid ports to control the flow of fluid through said valves, and a plurality of coils mounted externally of said valves to transport fluids to and from the valves, thereby providing means for washing out the sample flow system while the valve is injecting a sample into the reaction flow system.

2. An apparatus for rapid analysis of a plurality of fluid samples, comprising:
   a. a sample flow system for introducing samples sequentially into the system comprising a device for holding a series of samples, means for automatically indexing said device to advance each sample into position in sequence for being introduced into the system, a wash solution reservoir, and means for introducing said samples and wash solution into the system;
   b. a reaction flow system for reacting said fluid samples with reagent and for analyzing the reacted samples comprising a sample solvent reservoir, at least one reagent reservoir, a mixer for mixing sample and reagent, means for transferring solvent and reagent from the reservoirs to the mixer and for providing a continual flow of fluid at a constant rate through the reaction flow system when the apparatus is in operation, a reaction coil connected to the mixer for reacting sample and reagent, and means for analyzing the reacted samples and for recording the analyses; and
   c. a stream sampling valve common to both (a) and (b) for transferring a known volume of sample only from (a) to (b), comprising a plurality of four-way valves, each having a plurality of ports and an element slidably mounted for movement within said valves, said elements being provided with fluid conducting conduits adapted to register with the aforesaid ports to control the flow of fluid through said valves, and a plurality of coils mounted externally of said valves to transport fluid to and from said valves, thereby providing means for the sample flow system to be washed out while the valve is transferring a sample into the reaction flow system.

3. An apparatus for rapid analyses of a plurality of fluid samples, comprising:
   a. a sample flow system for introducing samples sequentially into the system comprising a device for holding a series of samples, means for automatically indexing said device to advance each sample into position in sequence for being introduced into the system, a wash solution reservoir, a probe for introducing sample and wash solution into the system, a pump and conduit connected to said probe to provide continuous suction for the probe and means operable automatically to immerse the probe alternately into the wash solution and into each automatically indexed sample to form a flowing stream of samples separated from each other by successive segments of air, wash solution, and air;
   b. a reaction flow system for reacting said fluid samples with reagent and for analyzing the reacted samples comprising a sample solvent reservoir, at least one reagent reservoir, a mixer for mixing a sample with reagent, conduits connecting said reservoirs with said mixer, pulse free pumps for delivering solvent and reagent from their respective reservoirs at a predetermined flow rate to the mixer and to the other parts of the system and for providing a continual flow of fluid at a constant rate through the reaction flow system when the apparatus is in operation, a reaction coil for reacting a sample and reagent, a conduit connecting the reaction coil to the mixer, and means for analyzing the reacted sample and for recording the analyses; and
   c. a stream sampling valve common to both (a) and (b) for taking out a (a) a measured volume of sample only and injecting it into (b), comprising a plurality of four-way valves, each having four ports and an element slidably mounted for movement within said valves, said elements being provided with fluid conducting conduits adapted to register with the aforesaid ports to control the flow of fluid through said valves and a plurality of coils mounted externally of and connected to the ports of said valves to transport fluids to and from said valves thereby providing means for the sample flow system to be washed out while the valve is transferring a sample into the reaction flow system.

4. The apparatus of claim 3 wherein the internal diameter of the conduits and coils in the stream sampling valve and in the reaction flow system ranges from 0.009 to 0.028 inches (32 to 22 AWG).

5. The apparatus of claim 4 wherein the internal diameter of the conduits and coils is 0.018 inches (26 AWG).

6. The apparatus of claim 4 wherein the streams sampling valve is provided with a timing means to activate it to transfer a known, predetermined volume of sample only from the sample flow system to the reaction flow system.

7. A method of analysis of a plurality of fluid samples, comprising:
   a. indexing a series of samples in sequence into sampling position;
   b. introducing the samples into a sample flow system in sequence;
   c. separating successive samples from each other in the sample flow system with individual segments of air, wash solution and air;
   d. energizing a stream sampling valve to remove a portion of each sample only and to transfer each of said portions to a reaction flow system in which fluid is flowing continually at a constant rate;
   e. mixing and reacting each sample with an appropriate reagent; and
   f. analyzing the reacted sample.

8. In a method of analysis of a plurality of fluid samples wherein the samples are sequentially transmitted into an apparatus to form a flowing stream wherein each sample is in sequence with the preceding and succeeding samples and each sample is separated from said preceding and succeeding samples by an intervening segment of air and wherein said air-segmented stream of samples is treated for analysis and then analyzed, the improvement which comprises removing from the aforesaid stream a measured volume of sample only, transferring said measured volume of each sample to a flowing stream of sample solvent, mixing and reacting each sample with an appropriate reagent and analyzing the reacted sample.

* * * * *

REEXAMINATION CERTIFICATE (234th)
United States Patent [19]
Stewart et al.

[11] B1 4,013,413
[45] Certificate Issued Aug. 28, 1984

[54] APPARATUS AND METHOD FOR RAPID ANALYSES OF PLURALITY OF SAMPLES

[75] Inventors: Kent K. Stewart, Silver Spring; Gary R. Beecher, Laurel; Peter E. Hare, Takoma Park, all of Md.

[73] Assignee: The United States of America as represented by the Secretary of Agriculture, Washington, D.C.

Reexamination Request:
No. 90/000,437, Aug. 24, 1983

Reexamination Certificate for:
| | |
|---|---|
| Patent No.: | 4,013,413 |
| Issued: | Mar. 22, 1977 |
| Appl. No.: | 594,893 |
| Filed: | Jul. 10, 1975 |

[51] Int. Cl.³ .............. G01N 1/00; G01N 31/00; G01N 35/08
[52] U.S. Cl. .............................. 436/53; 422/64; 422/81; 422/82; 436/52
[58] Field of Search ............... 422/81, 82; 436/52, 436/53; 225/55

[56] References Cited
U.S. PATENT DOCUMENTS

| | | | |
|---|---|---|---|
| 3,096,157 | 7/1963 | Brown et al. | 23/232 |
| 3,139,755 | 7/1964 | Reinecke et al. | 73/422 |
| 3,224,486 | 12/1965 | Holl, Jr. et al. | 436/52 |
| 3,285,701 | 11/1966 | Robertson | 23/232 |
| 3,306,229 | 2/1967 | Smythe | 436/53 |
| 3,357,233 | 12/1967 | Roof | 73/23.1 |
| 3,501,961 | 3/1970 | Hable et al. | 73/422 GC |
| 3,625,655 | 12/1971 | Culp et al. | 23/253 R |
| 3,649,203 | 3/1972 | Schneider | 23/253 R |
| 3,667,915 | 6/1972 | Klein | 436/53 |
| 3,712,144 | 1/1973 | Kuzel et al. | 73/421 R |
| 3,846,074 | 11/1974 | Tulumello et al. | 23/230 R |
| 3,855,129 | 12/1974 | Abrahams et al. | 222/55 |
| 3,876,374 | 4/1975 | Burns | 23/230 R |
| 3,918,913 | 11/1975 | Stevenson et al. | 23/259 |

OTHER PUBLICATIONS

G. Nagy, Z. S. Feher and E. Pungor, Anal. Chim. Acta, 1970, 52, 47.
Z. S. Feher and E. Pungor, Anal. Chim. Acta, 1974, 71, 425.
Z. S. Feher, G. Nagy, K. Toth and E. Pungor, Analyst, 1974, 99, 699.
V. V. S. Eswara Dutt and H. A. Mottola, Anal. Chem. vol. 47, No. 2, Feb. 1975.
J. J. T. Gerding, H. J. M. Kempen, B. J. M. Lamers and M. H. Gerding, J. Chromatog., 1972, 66, 145.
J. D. Frantz and P. E. Hare, Annual Rept. Director Geophys. Lab, 1973, 1630, 704.
Stewart et al, Automated High Speed Analyses of Discrete Samples–The Use of Non–Segmented, Continuous Flow Stream. Federation Proc. vol. 33, No. 5, Part II, May 1974.
Cheminert Valves.

*Primary Examiner*—Michael S. Marcus

[57] ABSTRACT

An apparatus and method for automatically analyzing up to 150 samples per hour with high precision. Air segmentation and its concomitant limitations and drawbacks are eliminated by use of a novel stream sampling valve which transfers a predetermined volume of sample only from a sample flow system to a reaction flow system.

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3, 7 and 8 are determined to be patentable as amended.

Claims 4–6, dependent on an amended claim, are determined to be patentable.

New claims 9–22 are added and determined to be patentable.

1. An apparatus for rapidly analyzing a plurality of fluid samples, comprising a *segmented* sample flow system for introducing samples into the apparatus, [a reaction flow system into the apparatus,] a reaction flow system for introducing reagent and sample solvent into the apparatus and for reacting reagent and sample and analyzing the reacted sample, said reaction flow system having means for providing a continual flow of fluid at a constant rate through said system when the apparatus is in operation, and a stream sampling valve common to both the sample flow system and the reaction flow system for transferring a volume of sample only from the sample flow system to the reaction flow system, comprising a plurality of four-way valves, each having a plurality of ports and an element slidably mounted for movement within said valves, said elements being provided with fluid conducting conduits adapted to register with the aforesaid ports to control the flow of fluid through said valves, and a plurality of coils mounted externally of said valves to transport fluids to and from the valves, [thereby] *said valve* providing means for washing out the sample flow system while the valve is injecting a sample into the reaction flow system.

2. An apparatus for rapid analysis of a plurality of fluid samples, comprising:
  a. a sample flow system for introducing samples sequentially into the system comprising a device for holding a series of samples, means for automatically indexing said device to advance each sample into position in sequence for being introduced into the system, a wash solution reservoir, and means for introducing said samples and wash solution into the system;
  b. a reaction flow system for reacting said fluid samples with reagent and for analyzing the reacted samples comprising a sample solvent reservoir, at least one reagent reservoir, a mixer for mixing sample and reagent, means for transferring solvent and reagent from the reservoirs to the mixer and for providing a continual flow of fluid at a constant rate through the reaction flow system when the apparatus is in operation, a reaction coil connected to the mixer for reacting sample and reagent, and means for analyzing the reacted samples and for recording the analyses; and
  c. a stream sampling valve common to both (a) and (b) for transferring a known volume of sample only from (a) to (b), comprising a plurality of four-way valves, each having a plurality of ports and an element slidably mounted for movement within said valves, said elements being provided with fluid conducting conduits adapted to register with the aforesaid ports to control the flow of fluid through said valves, and a plurality of coils mounted externally of said valves to transport fluid to and from said valves, [thereby] *said valve* providing means for the sample flow system to be washed out while the valve is transferring a sample into the reaction flow system.

3. An apparatus for rapid analyses of a plurality of fluid samples, comprising:
  a. a sample flow system for introducing samples sequentially into the system comprising a device for holding a series of samples, means for automatically indexing said device to advance each sample into position in sequence for being introduced into the system, a wash solution reservoir, a probe for introducing sample and wash solution into the system, a pump and conduit connected to said probe to provide continuous suction for the probe and means operable automatically to immerse the probe alternately into the wash solution and into each automatically indexed sample to form a flowing stream of samples separated from each other by successive segments of air, wash solution, and air;
  b. a reaction flow system for reacting said fluid samples with reagent and for analyzing the reacted samples comprising a sample solvent reservoir, at least one reagent reservoir, a mixer for mixing a sample with reagent, conduits connecting said reservoirs with said mixer, pulse free pumps for delivering solvent and reagent from their respective reservoirs at a predetermined flow rate to the mixer and to the other parts of the system and for providing a continual flow of fluid at a constant rate through the reaction flow system when the apparatus is in operation, a reaction coil for reacting a sample and reagent, a conduit connecting the reaction coil to the mixer, and means for analyzing the reacted sample and for recording the analyses; and
  c. a stream sampling valve common to both (a) and (b) for taking out a (a) a measured volume of sample only and injecting it into (b), comprising a plurality of four-way valves, each having four ports and an element slidably mounted for movement within said valves, said elements being provided with fluid conducting conduits adapted to register with the aforesaid ports to control the flow of fluid through said valves and a plurality of *c*oils mounted externally of and connected to the ports of said valves to transport fluids to and from said valves, [thereby] *said valves* providing means for the sample flow system to be washed out while the valve is transferring a sample into the reaction flow system.

7. A method of analysis of a plurality of fluid samples, comprising:
  a. indexing a series of samples in sequence into sampling position;
  b. introducing the samples into a sample flow system in sequence;

c. separating successive samples from each other in the sample flow system with individual segments of air, wash solution and air;
d. energizing a stream sampling valve to remove a portion of each sample only and to transfer each of said portions to a reaction flow system in which [fluid] *solvent* is flowing continually at a constant rate;
e. mixing and reacting each sample with an appropriate reagent; [and]
f. *maintaining the integrity of said sample portion between said transfer step and said mixing step; and*
g. analyzing the reacted sample.

8. In a method of analysis of a plurality of fluid samples wherein the samples are sequentially transmitted into an apparatus to form a flowing stream wherein each sample is in sequence with the preceding and succeeding samples and each sample is separated from said preceding and succeeding samples by an intervening segment of air and wherein said air-segmented stream of samples is treated for analysis and then analyzed, the improvement which comprises removing from the aforesaid stream a measured volume of sample only, transferring said measured volume of each sample to a non-gas-segmented flowing stream of sample solvent, mixing and reacting each sample with an appropriate reagent, *maintaining the integrity of said volume of sample between said transfer step and said mixing step,* and analyzing the reacted sample.

9. The apparatus of claims 2 or 3 wherein said reaction flow system includes means to maintain the integrity of said volume of sample as it flows from said valve to said mixer without air segmentation.

10. The apparatus of claims 1, 2 or 3 wherein said ports, coils, slidable elements and conduits in said valve define a plurality of passageways including a first passageway connectable to either said sample flow system or said reaction flow system; a second passageway connectable to said reaction flow system; a third passageway connectable to said sample flow system; wherein each passageway becomes a part of its respective system when connected thereto; and wherein said valve includes means to connect said first passageway to said sample flow system while connecting said second passageway to said reaction flow system; means to thereafter connect said first passageway to said reaction flow system while connecting said third passageway to said sample flow system when said first passageway contains said volume of sample only to thereby transfer said volume from said first passageway to said sample solvent in said reaction flow system, and to permit said sample flow system to be washed out through said third passageway when said volume of sample is being injected into said reaction flow system.

11. The apparatus of claim 1 wherein said reaction flow system comprises a reaction flow conduit connected to said valve, a reagent conduit connected to said reaction flow conduit downstream from said valve for the purpose of said introduction of reagent to react with said volume of sample to form said reacted sample.

12. The apparatus of claim 2 wherein said reaction flow system comprises a reaction flow conduit connected to said valve, a reagent conduit connected to said reaction flow conduit downstream from said valve for the purpose of said transfer of said reagent to react with said known volumes of sample to form said reacted samples.

13. The apparatus of claims 11 or 12 wherein said reaction flow system includes means to maintain the integrity of said volume of sample as it flows from said valve to the connection between said reaction flow conduit and reagent conduit without air segmentation.

14. The apparatus of claim 1 wherein said reaction flow system includes means to maintain the integrity of said volume of sample as it flows from said valve to said introduction of reagent without air segmentation.

15. The apparatus of claims 1, 2 or 3 wherein said means for providing a continual flow of fluid includes means to provide a flow rate of 0.1 to 25 ml per minute through said reaction flow system.

16. The method of claims 7 or 8 further comprising analyzing 60-150 samples per hour in said reaction flow system.

17. The method of claims 7 or 8 wherein said reaction flow system has a flow rate of 0.1 to 25 ml per minute.

18. *A method of analysis of a plurality of fluid samples, comprising:*
a. *indexing a series of samples in sequence into sampling position;*
b. *introducing the samples into a sample flow system in sequence;*
c. *separating successive samples from each other in the sample flow system with individual segments of air, wash solution and air;*
d. *energizing a stream sampling valve to remove a portion of each sample only and to transfer each of said portions to a reaction flow system in which sample solvent is flowing continually at a constant rate, to thereby form a continually flowing stream in which each of said portions is interspaced from one another by said solvent;*
e. *mixing and reacting each of said portions in said continually flowing stream with an appropriate reagent added to said continually flowing stream downstream from said valve to form reacted sample;*
f. *analyzing the reacted sample; and*
g. *maintaining the integrity of each of said portions as it flows from said valve to said mixing step without air segmentation.*

19. *In a method of rapid analysis of a plurality of fluid samples wherein the samples are sequentially transmitted into an apparatus to form a flowing stream wherein each sample is in sequence with the preceding and succeeding samples by an intervening segment of air and wherein said air-segmented stream of samples is treated for analysis and then analyzed, the improvement which comprises removing from the aforesaid stream a measured volume of sample only, transferring said measured volume of each sample to a flowing stream of sample solvent, mixing and reacting each of said measured volumes in said sample solvent with an appropriate reagent added to said sample solvent downstream from said transfer step to form reacted sample, analyzing the reacted sample, and maintaining integrity of said measured volume of sample as if flows from said transfer step to said mixing step without air segmentation.*

20. *A method for rapid analysis of a plurality of fluid samples, comprising:*
a. *indexing a series of samples in sequence into sampling position in a sample holding means;*
b. *introducing the samples from the sample holding means into a sample flow conduit in sequence by means of a sample introducing means;*
c. *introducing air and wash solution into said sample flow conduit by means of air-introducing means and wash solution-introducing means connected to said sample flow conduit to form a stream of samples in said sample flow conduit in which successive samples* are separated from one another by individual segments of air, wash solution and air;

d. energizing a stream sampling valve, which is connected to said sample flow conduit, to remove a portion of each sample only from said sample flow conduit and to transfer each of said portions to a reaction flow conduit also connected to said valve, in which sample solvent is flowing continually at a constant rate to thereby form a continually flowing stream of sample portions interspaced from one another by said sample solvent; wherein said reaction flow conduit includes means to introduce said solvent therein;

e. mixing and reacting each of said sample portions in said reaction flow conduit with reagents by means of a reagent conduit joined to said reaction flow conduit downstream from said valve to form reacted sample in said reaction flow conduit;

f. analyzing said reacted sample by means of an analyzer connected to said reaction flow conduit downstream from said reagent conduit;

g. maintaining the integrity of each of said portions as it flows from said valve to said mixing step without air segmentation;

wherein said valve includes first, second and third passageways connectable to said sample and reaction flow conduits in such a manner that a passageway becomes a part of a conduit when connected thereto; wherein said step of sample removal and transfer comprises connecting said first passageway to said sample flow conduit while connecting said second passageway to said reaction flow conduit; thereafter connecting said first passageway to said reaction flow conduit while connecting said third passageway to said sample flow conduit when said first passageway contains said portion of sample only to transfer said portion from said first passageway to said sample solvent in said reaction flow conduit, and to wash out said sample flow conduit through said third passageway while said portion of sample is being injected into said sample solvent in said reaction flow conduit.

21. In a method of analysis of a plurality of fluid samples wherein the samples are sequentially transmitted with air into a sample flow conduit in an apparatus to form a flowing stream in said conduit wherein each sample is in sequence with preceding and succeeding samples by an intervening segment of air, and wherein each of said samples is treated for analysis by adding appropriate reagent thereto from a reagent conduit connected to said apparatus to mix with said samples, wherein each of the samples is reacted with said reagent in a reaction coil connected to said apparatus to form reacted sample, and wherein said apparatus includes an analyzer so that said method includes the step of analyzing the reacted sample, the improvement which comprises removing from the sample flow conduit a measured volume of each sample only and transferring said measured volume to a stream of sample solvent flowing at a constant rate in a reaction flow conduit to thereby form a continually flowing stream in which each of said measured volumes is interspaced from one another by said sample solvent, wherein the removal and transfer steps are performed by energizing a stream sampling valve connected to said reaction flow conduit and said sample flow conduit, wherein said reagent conduit is connected to said reaction flow conduit downstream from said valve so that said method of analysis includes the step of adding said reagent to each of said measured volumes downstream from said valve to mix with said measured volumes, wherein said reaction coil is connected to said reaction flow conduit downstream from said reagent conduit so that said method of analysis includes the step of reacting said reagent with each of said measured volumes downstream from said reagent conduit to form said reacted sample, wherein said analyzer is connected to said reaction flow conduit downstream from said reaction coil so that said method of analysis includes the step of analyzing said reacted sample downstream from said reaction coil, wherein said method of analysis includes the step of maintaining the integrity of each of said measured volumes as it flows from said valve to said mixing step without air segmentation;

wherein said valve includes first, second and third passageways connectable to said sample and reaction flow conduits in such a manner that a passageway becomes a part of a conduit when connected thereto; wherein the sample removal and transfer steps comprise connecting said first passageway to said sample flow conduit while connecting said second passageway to said reaction flow conduit; thereafter connecting said first passageway to said reaction flow conduit while connecting said third passageway to said sample flow conduit when said first passageway contains said measured volume of sample only to transfer said measured volume from said first passageway to said sample solvent in said reaction flow conduit, and to wash out said sample flow conduit through said third passageway while said measured volume is being injected into said reaction flow conduit.

22. A method of analysis of a plurality of fluid samples comprising:

a. indexing a series of samples in sequence into sampling position;

b. introducing the samples into a sample flow system in sequence;

c. separating successive samples from each other in the sample flow system with individual segments of air, wash solution and air;

d. energizing a stream sampling valve to remove a portion of each sample only and to transfer each of said portions to a reaction flow system in which sample solvent is flowing continually at a constant rate, and to wash out said sample flow system through said valve while each of said portions is being transferred into said reaction flow system;

e. mixing and reacting each sample with an appropriate reagent; and f. analyzing the reacted sample.

* * * * *